US010183295B2

(12) United States Patent
Liu et al.

(10) Patent No.: US 10,183,295 B2
(45) Date of Patent: Jan. 22, 2019

(54) CONVECTIVE POLYMERASE CHAIN REACTION APPARATUS AND OPTICAL DETECTING METHOD THEREOF

(71) Applicant: INDUSTRIAL TECHNOLOGY RESEARCH INSTITUTE, Hsinchu (TW)

(72) Inventors: Tseng-Huang Liu, Kaohsiung (TW); Kuo-Hsing Wen, Jhudong Township (TW); Pei-Shin Jiang, Hsinchu (TW); Jie-Len Huang, Hsinchu (TW); Ting-Hsuan Chen, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 52 days.

(21) Appl. No.: 15/588,043

(22) Filed: May 5, 2017

(65) Prior Publication Data
US 2018/0104696 A1    Apr. 19, 2018

Related U.S. Application Data

(60) Provisional application No. 62/409,387, filed on Oct. 18, 2016.

(30) Foreign Application Priority Data

Dec. 27, 2016    (TW) .............................. 105143407 A

(51) Int. Cl.
| | | |
|---|---|---|
| C12Q 1/68 | (2018.01) | |
| B01L 7/00 | (2006.01) | |
| C12Q 1/686 | (2018.01) | |
| G01N 21/00 | (2006.01) | |

(52) U.S. Cl.
CPC ................ B01L 7/52 (2013.01); B01L 7/525 (2013.01); C12Q 1/686 (2013.01); G01N 21/00 (2013.01); *B01L 2300/0654* (2013.01); *B01L 2300/0681* (2013.01); *B01L 2300/0832* (2013.01); *B01L 2300/18* (2013.01); *B01L 2400/0445* (2013.01)

(58) Field of Classification Search
CPC .............. B01L 7/52; B01L 2300/0654; B01L 2300/0832; C12Q 1/686; C12Q 2563/107
See application file for complete search history.

(56) References Cited

U.S. PATENT DOCUMENTS

| | | | |
|---|---|---|---|
| 6,524,532 B1 * | 2/2003 | Northrup | ............. B01J 19/0046 422/52 |
| 8,187,813 B2 | 5/2012 | Chen et al. | |
| 9,074,250 B2 | 7/2015 | Bird et al. | |
| 2013/0109021 A1 | 5/2013 | Hwang | |

FOREIGN PATENT DOCUMENTS

| | | |
|---|---|---|
| CN | 101983236 A | 3/2011 |
| CN | 103649301 B | 3/2015 |
| CN | 103732757 B | 11/2015 |

OTHER PUBLICATIONS

Agrawal et al., "A Pocket-Sized Convective PCR Thermocycler", Angewandte Chemie International Edition, vol. 46, 2007, pp. 4316-4319 (Total No. pp. 5).
Chang et al., "A thermally baffled device for highly stabilized convective PCR", Biotechnology Journal, vol. 7, 2012, pp. 662-666.
Chou et al., "Rapid DNA amplification in a capillary tube by natural convection with a single isothermal heater", BioTechniques, vol. 50, No. 1, Jan. 2011, pp. 52-57.
Hsieh et al., "A real-time convective PCR machine in a capillary tube instrumented with a CCD-based fluorometer", Sensors and Actuators B, vol. 183, 2013, pp. 434-440.
Krishnan et al., "PCR in a Rayleigh-Bénard Convection Cell", Science, vol. 298, Oct. 25, 2002, p. 793.
Lin et al., "Development of a TaqMan Probe-Based Insulated Isothermal Polymerase Chain Reaction (iiPCR) Assay of Detection of *Fusarium oxysporum* f. sp. cubense Race 4", PLOS One, Jul. 22, 2016, pp. 1-13.
Priye et al., "Microscale Chaotic Advection Enables Robust Convective DNA Replication", Analytical Chemistry, vol. 85, 2013, pp. 10536-10541.
Tsai et al., "Detection of white spot syndrome virus by polymerase chain reaction performed under insulated isothermal conditions", Journal of Virological Methods, vol. 181, 2012, pp. 134-137.
Wheeler et al., "Convectively Driven Polymerase Chain Reaction Thermal Cycler", 7th International Conference on Miniaturized Chemical and Biochemical Analysis Systems, Oct. 5-9, 20013, pp. 1133-1135.
Zhang et al., "A Convenient Nucleic Acid Test on the Basis of the Capillary Convective PCR for the On-Site Detection of Enterovirus 71", The Journal of Molecular Diagnostics, vol. 16, No. 4, Jul. 2014, pp. 452-458.

* cited by examiner

*Primary Examiner* — David C Thomas
(74) *Attorney, Agent, or Firm* — Birch, Stewart, Kolasch & Birch, LLP

(57) ABSTRACT

A convective polymerase chain reaction apparatus includes a tube, a temperature control unit, at least one light source and a sensor. The tube includes a cavity used to contain a reaction solution. The reaction solution has a liquid level measured from a bottom of the cavity to a top surface of the reaction solution. The temperature control unit is disposed adjacent to the tube for controlling the temperature of the reaction solution. The at least one light source provides a light beam passing through an incident portion of the tube to excite the reaction solution emitting a fluorescent light. The incident portion is located at a height greater than ½ of a liquid level. The sensor is adjacent to the tube for detecting the excited fluorescence. The light beam has an incident direction forming a non-straight angle with a long axis of the tube.

10 Claims, 4 Drawing Sheets

CONVECTIVE POLYMERASE CHAIN REACTION APPARATUS AND OPTICAL DETECTING METHOD THEREOF

This application claims the benefit of U.S. provisional application Ser. No. 62/409,387 filed Oct. 18, 2016, and Taiwan application Serial No. 105143407, filed Dec. 27, 2016, the disclosure of which are incorporated by reference herein in its entirety.

TECHNICAL FIELD

The disclosure relates in general to a polymerase chain reaction (PCR) apparatus and a detecting method thereof, and more particularly to a convective polymerase chain reaction (cPCR) apparatus and an optical detecting method thereof.

BACKGROUND

Polymerase chain reaction (PCR) is a molecular biology technology used for expanding specific deoxyribonucleic acid (DNA) or ribonucleic acid (RNA) segments. Typical polymerase chain reaction apparatus repeats a thermal cycling procedure to perform a repetitive process of heating and cooling using a thermocycler. Thermal energy is gradually transferred to a reaction tube through a metal block to tuning the reacting temperature, such that the DNA or RNA segments can react undergo at three different temperature conditions, namely, denaturation (95° C.), adhesion (45° C.-65° C.) and extension (72° C.). Conventionally, the thermal cycling procedure is performed through multi-level indirect heating, which not only consumes a large amount of time but also requires a large machine volume, the detection efficiency of the traditional PCR and the application scope thereof may thus be rather limited.

A convective polymerase chain reaction (cPCR), is a special type of PCR based on the principle of thermal convection, the reaction vessel containing a reaction solution is directly heated, such that the reaction solution generates temperature gradient and causes thermal convection. The reaction solution can move around the reaction vessel, and the temperature of the reaction solution can keep changing along the convection path of the reaction solution, whereby the expansion of the nucleic acid can be completed along with the convection path of the reaction solution instead of changing the temperature of the whole reaction solution. The nucleic acid expansion time thus can be shorten, the apparatus and instrument for performing the polymerase chain reaction can be simplified and the detection cost may be reduced. Currently the convective polymerase chain reaction apparatus includes a reaction vessel formed of plastic tube or glass capillary, a light source disposed under the bottom of the tube and providing a light beam to excite the fluorescent reagent inside the tube to generate a fluorescence signal, and a detector used to detect the fluorescence signal to achieve the object of monitoring the polymerase chain reaction.

However, since the reaction solution of polymerase chain reaction typically includes a biological specimen (such as the whole blood of an organism) that may has a very complicated ingredients, thus most residues of the reaction solution (such as protein, blood cells) may decapitate at the bottom of the capillary to interfered and obstructed the optical path of the incident light beam and the excited fluorescence signal. Consequently, the light beam cannot pass through the bottom of the tube to excite the fluorescent reagent inside the tube, the fluorescence signal cannot be received by the detector on the tube-wall, and the performance and the process control of the polymerase chain reaction is severely affected.

Therefore, there is a need to provide an advanced convective polymerase chain reaction apparatus and an optical detecting method thereof to obviate the drawbacks and problems encountered from the prior art.

SUMMARY

According to one embodiment, a convective polymerase chain reaction (cPCR) apparatus is provided. The convective polymerase chain reaction apparatus includes a tube, a temperature control unit, at least one light source and a sensor. The tube includes a cavity used to contain a reaction solution. The reaction solution has a liquid level measured from a bottom of the cavity to a top surface of the reaction solution. The temperature control unit is disposed adjacent to the tube for controlling the temperature of the reaction solution. The at least one light source provides a light beam passing through an incident portion of the tube to reach and excite the reaction solution to emit a fluorescent light, wherein the incident portion is located at a height greater than ½ of the liquid level measured from the bottom of the cavity. The sensor is disposed adjacent to the tube for detecting the excited fluorescence. The light beam has an incident direction forming a non-straight angle with a long axis of the tube.

According to another embodiment, an optical detecting method for a convective polymerase chain reaction apparatus is provided. The optical detecting method for includes following steps: Firstly, a tube having a cavity used to contain a reaction solution is provided, wherein the reaction solution has a liquid level measured from a bottom of the cavity to a top surface of the reaction solution. Next, a light beam passing through an incident portion of the tube is provided to reach and excite the reaction solution to emit a fluorescent light, wherein the incident portion is located at a height greater than ½ of the liquid level measured from the bottom of the cavity. Then, a sensor is provided adjacent to the tube for sensing the excited fluorescence, wherein the light beam has an incident direction forming a non-straight angle with a long axis of the tube.

A convective polymerase chain reaction apparatus and an optical detecting method thereof are disclosed in the embodiments of the present disclosure. By flexibly adjusting the relative position between the sensor and the position at which the light beam incident into the reaction cavity in which the convective polymerase chain reaction carried out, the reacted fluorescence signal received by the sensor can be maximized, and the problems encountered in the generally known technology that the optical path of the sensor is interfered with and obstructed when the light source is disposed at the bottom of the reaction cavity can be resolved. Meanwhile, by adjusting the cavity, the sensor and the incident angle of the light beam, the space utilization of the convective polymerase chain reaction apparatus is more efficient, and the volume miniaturization of the convective polymerase chain reaction apparatus can be achieved.

The above and other aspects of the invention will become better understood with regard to the following detailed description of the preferred but non-limiting embodiment(s). The following description is made with reference to the accompanying drawings.

Figure 1A:
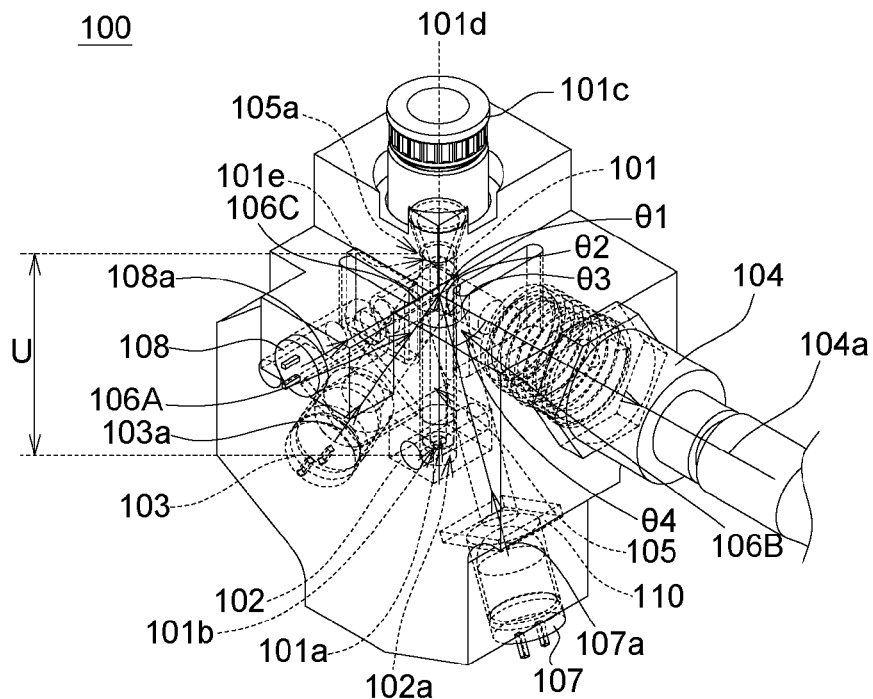
FIG. 1A is a perspective view illustrating a partial structure of a convective polymerase chain reaction apparatus according to an embodiment of the present specification.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

A convective polymerase chain reaction apparatus and an optical detecting method thereof are disclosed in the embodiments of the present specification. By applying the convective polymerase chain reaction apparatus and the optical detecting method thereof not only resolve the generally-known problems due to interference and obstruction of the biological specimen occurring in the optical path of the sensor but also minimizes the volume of the convective polymerase chain reaction apparatus. For the object, technical features and advantages of the present disclosure to be more easily understood by anyone ordinary skilled in the technology field, a number of exemplary embodiments are disclosed below with detailed descriptions and accompanying drawings.

It should be noted that the embodiments disclosed in the present specification are for exemplary and explanatory purposes only, not for limiting the scope of protection of the invention. The invention can be implemented by using other features, elements, methods and parameters. The embodiments are merely for illustrating the technical features of the invention, not for limiting the scope of protection. Anyone skilled in the technology field of the invention will be able to make suitable modifications or changes based on the specification disclosed below without breaching the spirit of the invention. Designations common to the accompanying drawings are used to indicate identical or similar elements.

Figure 1B:
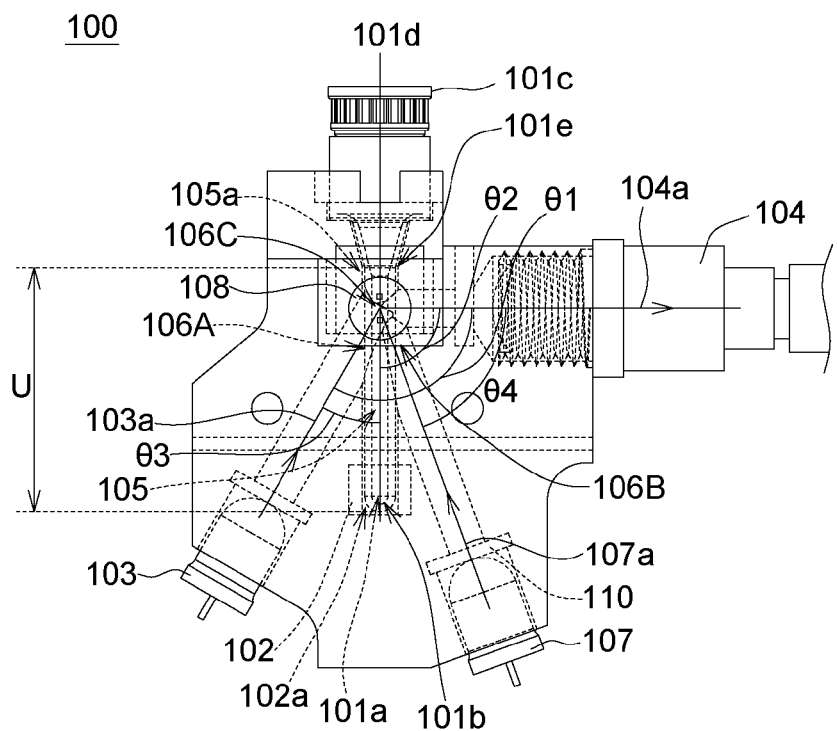
FIG. 1B is a side view illustrating a partial structure of the convective polymerase chain reaction apparatus of FIG. 1A.

Refer to FIG. 1A and FIG. 1B. FIG. 1A is a perspective view illustrating a partial structure of a convective polymerase chain reaction apparatus 100 according to an embodiment of the present specification. FIG. 1B is a side view illustrating a partial structure of the convective polymerase chain reaction apparatus 100 of FIG. 1A. The convective polymerase chain reaction apparatus 100 at least includes a tube 101, a temperature control unit 102, a light source 103 and a sensor 104.

In some embodiments of the present specification, the tube 101 is a translucent long tube formed of plastics or glass, such as a capillary. The tube 101 includes a cavity 101a used to contain a reaction solution 105. The reaction solution 105 contained in the cavity 101a has a liquid level U measured from a bottom 101b of the cavity 101a to a top surface 105a of the reaction solution 105.

The temperature control unit 102 is disposed adjacent to the tube 101 for controlling the temperature of the reaction solution 105. In some embodiments of the present specification, the temperature control unit 102 is designed to have a heating block capable of accommodating of the tube 101. The shape of the temperature control unit 102 is a groove 102a. The shape and size of the groove 102a are similar to that of the tube 101, such that the temperature control unit 102 can match the tube 101 to efficiently transfer the heat and reduce energy loss.

In the present embodiment, the temperature control unit 102 includes a metal heating block tightly surrounds the bottom of the tube 101 formed of plastic capillary for transferring the heat to the reaction solution 105 disposed inside the plastic capillary and is capable of maintaining the temperature of the bottom of the tube 101 at 90° C. The upper cover 101c of the tube 101 can be an open cover capable of maintaining the top of the tube 101 having a temperature at 50° C. Thus, a temperature gradient which is hot at the bottom and cold at the top can be formed, and the DNA or RNA of the reaction solution 105 disposed inside the tube 101 can be expanded through continuous temperature cycling.

The light source 103, which can be realized by a light emitting diode (LED) die, a halogen lamp, a tritium gas lamp, a xenon lamp, a laser source or any combination thereof, provides a light beam 103a having a special colored light. The light beam 103a passes an incident portion 106A of the tube 101 located at a height greater than ½ of a liquid level (that is, greater than ½ U) measured from a bottom 101b of the cavity 101a to a top surface of the reaction solution to reach and excite the reaction solution 105 to emit a fluorescent light 105. Different types of the reaction solution 105 that include type of biological specimens may have different sediments. To avoid the optical path being interfered by the sediments precipitating at the bottom 101b of the cavity, the incident portion 106A of the light source 103 is disposed at a height greater than ½ of the liquid level (that is, greater than ½ U) measured from the bottom 101b of the cavity 101a to the liquid level. The incident portion 106A is disposed at a height where the fluorescent product has a denser distribution, such that better detection effect can be achieved.

In an embodiment of the present specification, the light source 103, which can be realized by a monochromatic LED die, provides a red light beam having a wavelength substantially ranging from 600 nanometers (nm) to 750 nm, a green light beam having a wavelength substantially ranging from 500 nm to 570 nm or a blue light beam having a wavelength substantially ranging from 420 nm to 500 nm. In another embodiment of the present specification, the light source 103 can be realized by a white LED die, and a filter 110 interposed between the light source 103 and the tube 101, which can filter off a portion of the white light emitted by the light source 103 to allow another portion the light beam having a specific wavelength passing through the filter 110 and the tube 101 to reach the reaction solution 105. Through the selection (replacement) of the filter 110, one single light source 103 can provide polychromatic light beams 103a.

In some embodiments of the present specification, the position of the light source 103 with respect to the cavity 101a of the tube 101 can be adjusted according to the top surface 105a of the reaction solution 105. In the present embodiment, the reaction solution 105 contained in the cavity 101 of the tube 101 has a fixed volume, and the top surface 105a of the reaction solution 105 has the same height which can be denoted with a scale 101e. In other words, the top surface 105a of the reaction solution 105 and the position of the light source 103 with respect to the cavity 101a of the tube 101 can be relatively fixed at the scale 101e marked on the tube 101.

The sensor 104 is disposed adjacent to the tube 101 for detecting and sensing the fluorescence of the reaction solution 105 excited by the light beam 103a. In an embodiment of the present specification, the sensor 104 may include a photodiode for converting the received fluorescence intensity into a current signal or a voltage signal. In another embodiment of the present specification, the sensor 104 may include an optical fiber for transmitting the received fluorescence signal to a photoelectric conversion apparatus disposed inside or outside the convective polymerase chain reaction apparatus 100 for subsequent signal processing.

The sensor 104 is disposed corresponding to the light source 103 and the tube 101. In an embodiment of the present specification, the sensor 104 has a light receiving direction 104a forming an angle substantially ranging from 60° to 180° with an incident direction of the light beam 103a (indicated by an arrow sign). Besides, the light receiving direction 104a of the sensor 104 forms a non-straight angle with a long axis 101d of the tube 101. The incident direction of the light beam 103a provided by the light source 103 forms a non-straight angle ⊖3 with the long axis 101d of the tube 101.

In the present embodiment, the angle ⊖1 formed by the light receiving direction 104a of the sensor 104 and the incident direction of the light beam 103a is substantially equivalent to 120°; the angle ⊖2 formed by the light receiving direction 104a of the sensor 104 and the long axis 101d of the tube 101 is substantially equivalent to 90°; the angle ⊖3 formed by the incident direction of the light beam 103a and the long axis 101d of the tube 101 is substantially equivalent to 30°; the incident direction of the light beam 103a, the light receiving direction 104a of the sensor 104 and the long axis 101d of the tube 101 are on the same plane.

In some embodiments of the present specification, the convective polymerase chain reaction apparatus 100 may further include other light sources, such as light sources 107 and 108, which respectively provide light beams 107a and 108a. The wavelengths of the light beams 107a and 108a can be the same as or different from the wavelength of the light beam 103a. In the present embodiment, the light beam 107a provided by the light source 107 passes through an incident portion 106B of the tube 101 located at a height greater than ½ of the liquid level (that is, greater than ½ U) measured from the bottom 101b of the cavity 101a to the top surface of the reaction solution to reach the reaction solution 105. The light beam 108a provided by the light source 108 passes through an incident portion 106C of the tube 101 located at a height greater than ½ of the liquid level (that is, greater than ½ U) measured from the bottom 101b of the cavity 101a to the top surface of the reaction solution to reach the reaction solution 105. It should be noted that in the present embodiment, every two of the incident directions of the light beam 108a, the light receiving direction 104a of the sensor 104 and the long axis 101d of the tube 101 are orthogonal to each other and are not disposed on the same plane. To put it in greater details, the light receiving direction 104a of the sensor 104 is substantially perpendicular to the incident direction of the light beam 108a, and the incident direction of the light beam 108a is substantially perpendicular to the long axis 101d of the tube 101.

In an embodiment, the light receiving direction 104a of the sensor 104, the long axis 101d of the tube 101 and the incident directions of the light beam 103a and 107a are on the same plane. The angle ⊖4 formed by the light receiving direction 104a of the sensor 104 and the incident direction of the light beam 107a is substantially equivalent to 60°. The angle formed by the incident direction of the light beam 107a and the long axis 101d of the tube 101 is substantially equivalent to 30°.

Figure 2:
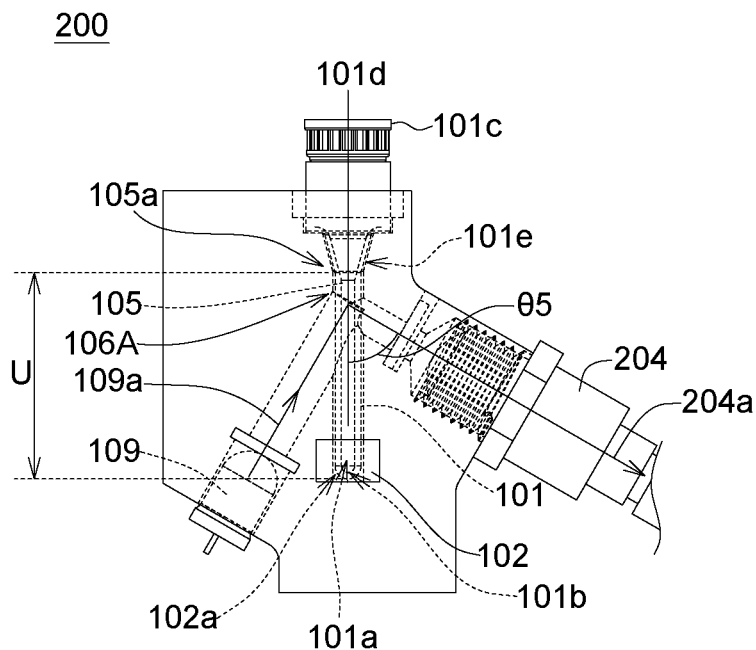
FIG. 2 is a side view illustrating a partial structure of a convective polymerase chain reaction apparatus according to another embodiment of the present specification.
Figure 3A:
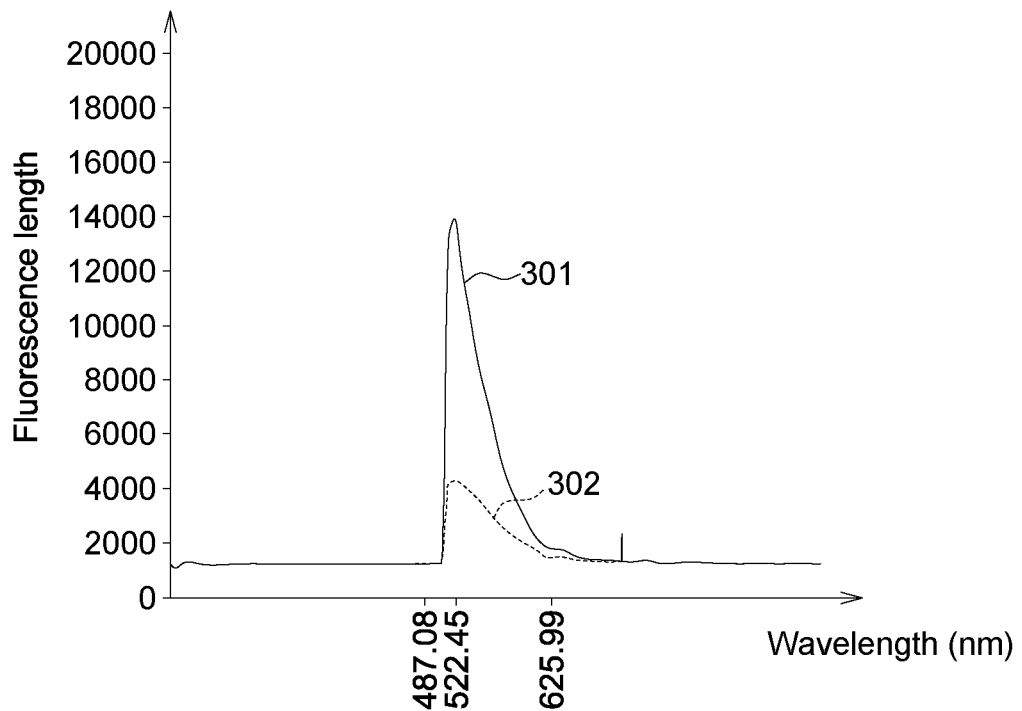
FIG. 3A to FIG. 3D are relationship diagrams of fluorescence intensity vs wavelength obtained after a convective polymerase chain reaction is performed, wherein fluorescence intensity is measured by a sensor, the light sources are disposed at different angles and two types of reaction solution are used, one reaction solution contains a specimen of whole blood and the other reaction solution contains pure water only.
Figure 3B:
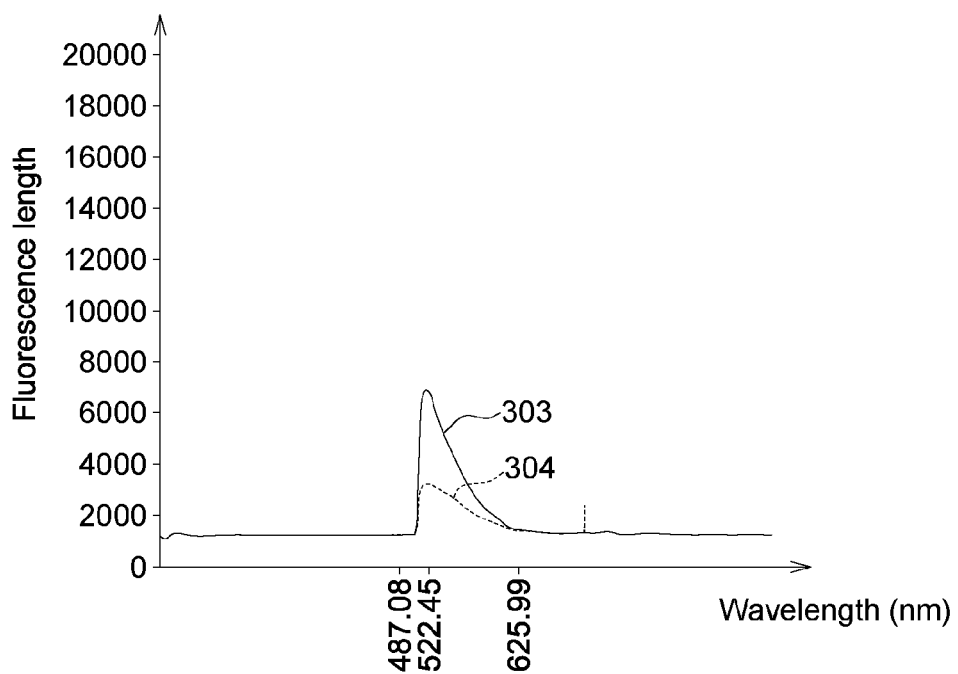
Figure 3C:
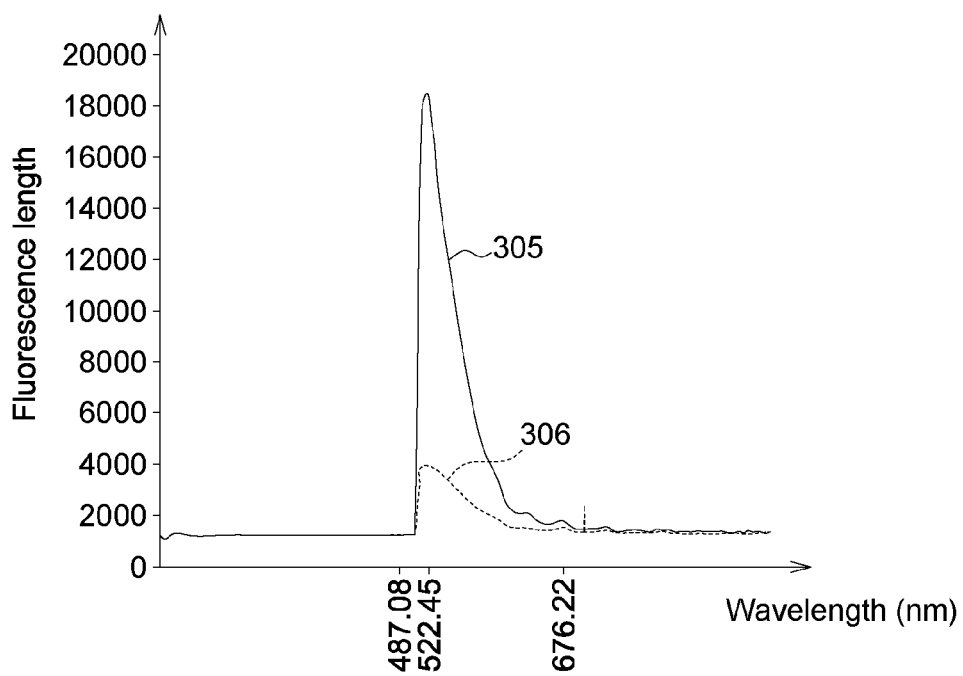
Figure 3D:
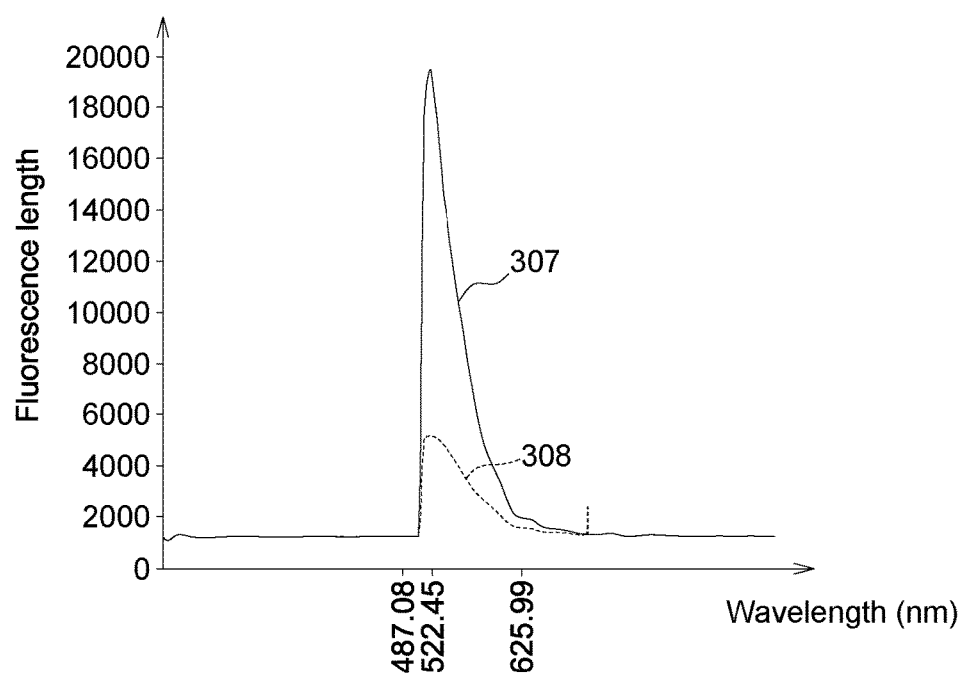

It should be noted that, relative positions between the sensor 104, the tube 101 and the light sources 103, 107 and 108 are not limited to the above exemplifications. For example, in some other embodiments of the present specification, the light receiving direction 104a of the sensor 204 and the long axis 101d of the tube 101 can form a non-right angle. Referring to FIG. 2, FIG. 2 is a side view illustrating a partial structure of a convective polymerase chain reaction apparatus 200 according to another embodiment of the present specification. The structure of the convective polymerase chain reaction apparatus 200 is similar to that of the convective polymerase chain reaction apparatus 100 except that the convective polymerase chain reaction apparatus 200 further includes a light source 109, and the light receiving direction 204a of the sensor 204 forms an angle ⊖5 substantially equivalent to 60° with the long axis 101d of the tube 101. In the present embodiment, the light receiving direction 204a of the sensor 204, the long axis 101d of the tube 101 and the incident direction of the light beam 109a are on the same plane; and the light receiving direction 204a of the sensor 204 is perpendicular to the incident direction of the light beam 109a.

Subsequently, various convective polymerase chain reactions using two types of reaction solution 105 and the light sources 103, 107, 108 and 109 of FIG. 1A, FIG. 1B and FIG. 2 that are disposed at different angles are performed, and the fluorescence intensity of the reaction solutions 105 are measured by the sensor 104 to verify the optical detection effect of the convective polymerase chain reaction apparatus 100, wherein one reaction solution 105 contains a specimen of whole blood and the other reaction solution 105 contains pure water only.

Refer to FIG. 3A to FIG. 3D. The curves 301 and 302 of FIG. 3A respectively illustrate the fluorescence intensity of two different convective polymerase chain reactions using two types of reaction solution 105 with the light source 103 and measured by the sensor 104. The curves 303 and 304 of FIG. 3B respectively illustrate the fluorescence intensity of two different convective polymerase chain reactions using two types of reaction solution 105 with the light source 107 and measured by the sensor 104. The curves 305 and 306 of FIG. 3C respectively illustrate the fluorescence intensity of two different convective polymerase chain reactions using two types of reaction solution 105 with the light source 108 and measured by the sensor 104. The curves 307 and 308 of FIG. 3D respectively illustrate the fluorescence intensity of two different convective polymerase chain reactions using two types of reaction solution 105 with the light source 109 and measured by the sensor 104. Wherein the two types of reaction solution 105, one contains a specimen of whole blood and the other contains pure water only.

The detection results illustrated in FIG. 3A, FIG. 3B, FIG. 3C and FIG. 3D show the facts that the convective polymerase chain reactions using two types of reaction solution 105 and different light sources 103, 107, 108 and 109 having different incident directions are carried out, the fluorescence signals (illustrated in curves 301, 303, 305, 307) of the convective polymerase chain reaction measured by the sensor 104 and using the reaction solution 105 containing a specimen of whole blood are significantly different from the fluorescence signals (illustrated in curves 302, 304, 306, 308) measured by the sensor 104 and using the reaction solution 105 containing pure water. Therefore, after the background value of the fluorescence signal of pure water is deducted, the fluorescence signal of actual polymerase chain reaction can be obtained. This implies that by adjusting relative position between the sensor and the position at which the light beam reaches the cavity of the convective polymerase chain reaction, the problems encountered in the generally known technology due to sediments interference and obstruction of the biological specimens that occurs on the sensing optical path can be resolved.

According to above disclosure, a convective polymerase chain reaction apparatus and an optical detecting method thereof are provided in embodiments of the present specification. By flexibly adjusting the relative position between the sensor and the position at which the light beam reaches the reaction cavity in the convective polymerase chain reaction, the reaction fluorescence signal received by the sensor is evident, and the problems encountered in the generally known technology due to the interference and obstruction occurring at the optical path of the sensor when the light source is disposed at the bottom of the reaction cavity can be resolved. Meanwhile, by adjusting the cavity, the sensor and the incident angle of the light beam, the space utilization of the convective polymerase chain reaction apparatus is more efficient, and the volume miniaturization of the convective polymerase chain reaction apparatus can be achieved.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A convective polymerase chain reaction (cPCR) apparatus, comprising:
    a tube having a cavity used to contain a reaction solution, wherein the reaction solution has a liquid level measured from a bottom of the cavity to a top surface of the reaction solution;
    a temperature control unit disposed adjacent to the tube for controlling the temperature of the reaction solution;
    at least one light source used to provide a light beam passing through an incident portion of the tube to reach and excite the reaction solution to emit a fluorescent light, wherein the incident portion is located at a height greater than ½ of the liquid level measured from the bottom of the cavity; and
    a sensor disposed adjacent to the tube for detecting the excited fluorescence;
    wherein, the at least one light source has an incident direction forming a non-straight angle with a long axis of the tube.

2. The convective polymerase chain reaction apparatus according to claim 1, further comprising a filter disposed between the at least one light source and the tube for filtering off a portion of the light beam to allow the other portion of the light beam having a specific wavelength passing through the incident portion to reach the reaction solution.

3. The convective polymerase chain reaction apparatus according to claim 1, wherein the sensor has a light receiving direction forming an angle substantially ranging from 60° to 180° with the incident direction of the at least one light source.

4. The convective polymerase chain reaction apparatus according to claim 3, wherein the long axis of the tube, the light receiving direction and the incident direction of the light at least one light source are on the same plane.

5. The convective polymerase chain reaction apparatus according to claim 3, wherein the long axis of the tube, the light receiving direction and the incident direction of the at least one light source are not on the same plane.

6. The convective polymerase chain reaction apparatus according to claim 5, wherein every two of the long axis of the tube, the light receiving direction and the incident direction of the at least one light source are orthogonal to each other.

7. The convective polymerase chain reaction apparatus according to claim 3, wherein the long axis of the tube form a non-straight angle with the light receiving direction.

8. The convective polymerase chain reaction apparatus according to claim 7, wherein the light receiving direction is perpendicular to the incident direction of the light at least one light source.

9. An optical detecting method of a convective polymerase chain reaction apparatus, comprising:
    providing a tube having a cavity used to contain a reaction solution, wherein the reaction solution has a liquid level measured from a bottom of the cavity to a top surface of the reaction solution;
    providing a light beam emitted from at least one light source passing through an incident portion of the tube to reach and excite the reaction solution to emit a fluorescent light, wherein the incident portion is located at a height greater than ½ of the liquid level measured from the bottom of the cavity; and
    providing a sensor disposed adjacent to the tube for receiving the excited fluorescence;
    wherein, the at least one light source has an incident direction forming a non-straight angle with a long axis of the tube.

10. The method according to claim 9, wherein the sensor has a light receiving direction forming an angle substantially ranging from 60° to 180° with the incident direction of the at least one light source.

* * * * *